(12) United States Patent
Hibner

(10) Patent No.: US 8,241,299 B2
(45) Date of Patent: Aug. 14, 2012

(54) BIOPSY MARKER DELIVERY CONFIGURED TO RETAIN MARKER PRIOR TO INTENDED DEPLOYMENT

(75) Inventor: John A. Hibner, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 22 days.

(21) Appl. No.: 12/603,864

(22) Filed: Oct. 22, 2009

(65) Prior Publication Data

US 2011/0098595 A1  Apr. 28, 2011

(51) Int. Cl.
*A61B 17/00* (2006.01)
*A61D 1/04* (2006.01)

(52) U.S. Cl. ........................ 606/116; 600/562

(58) Field of Classification Search .......... 600/562–572; 606/167, 170, 180, 106–107, 116–117; 604/19, 604/27
See application file for complete search history.

(56) References Cited

U.S. PATENT DOCUMENTS

| | | | | |
|---|---|---|---|---|
| 3,015,332 A * | 1/1962 | Brecht | | 604/15 |
| 5,337,733 A * | 8/1994 | Bauerfeind et al. | | 600/139 |
| 5,526,822 A | 6/1996 | Burbank et al. | | |
| 5,647,846 A * | 7/1997 | Berg et al. | | 604/93.01 |
| 5,762,631 A * | 6/1998 | Klein | | 604/171 |
| 5,772,671 A * | 6/1998 | Harmon | | 606/117 |
| 5,810,769 A * | 9/1998 | Schlegel et al. | | 604/59 |
| 6,074,612 A * | 6/2000 | Sagstetter | | 422/512 |
| 6,086,544 A | 7/2000 | Hibner et al. | | |
| 6,228,055 B1 | 5/2001 | Foerster et al. | | |
| 6,371,904 B1 | 4/2002 | Sirimanne et al. | | |
| 6,993,375 B2 | 1/2006 | Burbank et al. | | |
| 6,996,433 B2 | 2/2006 | Burbank et al. | | |
| 7,044,957 B2 | 5/2006 | Foerster et al. | | |
| 7,047,063 B2 | 5/2006 | Burbank et al. | | |
| 7,229,417 B2 | 6/2007 | Foerster et al. | | |
| 2003/0109803 A1 | 6/2003 | Huitema et al. | | |
| 2003/0233101 A1* | 12/2003 | Lubock et al. | | 606/116 |
| 2004/0097981 A1* | 5/2004 | Selis | | 606/151 |
| 2005/0228311 A1 | 10/2005 | Beckman et al. | | |
| 2006/0052758 A1* | 3/2006 | Dewey | | 604/272 |
| 2007/0118048 A1 | 5/2007 | Stephens et al. | | |

OTHER PUBLICATIONS

U.S. Appl. No. 12/564,315, filed Sep. 22, 2009, confirmation No. 8120.

* cited by examiner

*Primary Examiner* — Rene Towa
(74) *Attorney, Agent, or Firm* — Frost Brown Todd LLC

(57) ABSTRACT

A biopsy marker delivery device is described. The delivery device can include a relatively flexible hollow tube, a pushing member such as a push rod disposed for sliding with the tube, and at least one marker disposed in the tube. The inner surface of the tube can be configured to engage the marker at spaced apart locations on the outer surface of the marker.

20 Claims, 8 Drawing Sheets

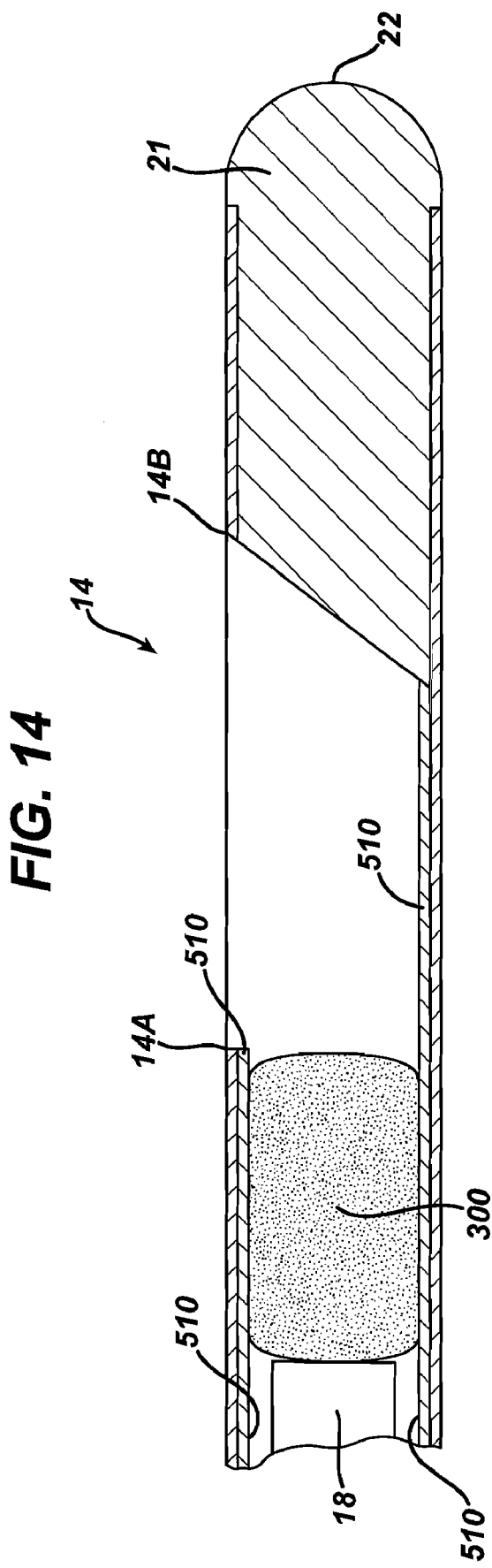

BIOPSY MARKER DELIVERY CONFIGURED TO RETAIN MARKER PRIOR TO INTENDED DEPLOYMENT

CROSS REFERENCE TO RELATED APPLICATIONS

This application cross references and incorporates by reference the following commonly assigned U.S. patent applications: Ser. No. 12/563,360 filed Sep. 21, 2009; and U.S. patent application Ser. No. 12/196,301 filed Aug. 22, 2008.

BACKGROUND

Biopsy samples have been obtained in a variety of ways in various medical procedures using a variety of devices. An exemplary biopsy device is the MAMMOTOME® brand device from Ethicon Endo-Surgery, Inc. of Cincinnati, Ohio. Biopsy devices may be used under stereotactic guidance, ultrasound guidance, MRI guidance, or otherwise.

Further exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2007/0118048, entitled "Remote Thumbwheel for a Surgical Biopsy Device," published May 24, 2007; U.S. Provisional Patent Application Ser. No. 60/869,736, entitled "Biopsy System," filed Dec. 13, 2006; U.S. Provisional Patent Application Ser. No. 60/874,792, entitled "Biopsy Sample Storage," filed Dec. 13, 2006; and U.S. Non-Provisional patent application Ser. No. 11/942,785, entitled "Revolving Tissue Sample Holder for Biopsy Device," filed Nov. 21, 2007. The disclosure of each of the above-cited U.S. patents, U.S. Patent Application Publications, U.S. Provisional Patent Applications, and U.S. Non-Provisional Patent Application is incorporated by reference herein.

In some settings, it may be desirable to mark the location of a biopsy site for future reference. For instance, one or more markers may be deposited at a biopsy site before, during, or after a tissue sample is taken from the biopsy site. Exemplary marker deployment tools include the MAMMOMARK®, MICROMARK®, and CORMARK® brand devices from Ethicon Endo-Surgery, Inc. of Cincinnati, Ohio. Further exemplary devices and methods for marking a biopsy site are disclosed in U.S. Pub. No. 2005/0228311, entitled "Marker Device and Method of Deploying a Cavity Marker Using a Surgical Biopsy Device," published Oct. 13, 2005; U.S. Pat. No. 6,996,433, entitled "Imageable Biopsy Site Marker," issued Feb. 7, 2006; U.S. Pat. No. 6,993,375, entitled "Tissue Site Markers for In Vivo Imaging," issued Jan. 31, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; U.S. Pat. No. 7,044,957, entitled "Devices for Defining and Marking Tissue," issued May 16, 2006; U.S. Pat. No. 6,228,055, entitled "Devices for Marking and Defining Particular Locations in Body Tissue," issued May 8, 2001; and U.S. Pat. No. 6,371,904, entitled "Subcutaneous Cavity Marking Device and Method," issued Apr. 16, 2002. The disclosure of each of the above-cited U.S. Patents and U.S. Patent Application Publications is incorporated by reference herein.

It may be desirable to deploy markers from a cannula type deployer into the biopsy site, such as a flexible tubular deployer. The marker should not unintentionally fall out of the deployer, and the force to deploy the marker should not be excessive.

In some instance, the biopsy marker disposed within the deployer may vary in size (possibly because of manufacturing variations, temperature, or humidity). For instance, in some cases a marker may be formed in part or in whole of a material that swells or otherwise changes size due to changes in temperature and/or humidity.

Applicant has recognized the desirability of providing a biopsy marker delivery device that accommodates markers which may vary in size over time, or which may vary from marker to marker due to manufacturing variations.

SUMMARY

In one non limiting aspect, the present invention provides a biopsy marker deployer, such as a flexible biopsy marker delivery device comprising a thin wall hollow tube having an internal lumen and carrying at least one biopsy marker within the lumen. The tube comprises at least one internal surface feature, such as a rib, engaging the at least one marker and extending along at least a portion of the length of the marker.

In one embodiment, the inside surface of the tube is configured to contact an outer surface of at least one marker, such as at discreet, spaced apart positions on an outer surface of the marker. In one embodiment, the inner surface of the tube is configured to contact a marker element at three or more circumferentially spaced apart locations around the outer surface of the marker.

According to one embodiment of the present invention, the marker deployer comprises a hollow tube having a plurality of longitudinally extending inner surface features, such as in the form of longitudinally extending ribs. By way of non-limiting example, the hollow tube may be extruded or molded to have a plurality of longitudinally extending ribs on an inner surface of the tube. The deployer tube can be configured to have at least three, and in one embodiment, at least four, longitudinally extending ribs that extend radially inwardly to simultaneously contact the marker element as the marker element is pushed distally through the tube.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 14 is a schematic illustration showing a partial cross section of a distal portion of a marker delivery device according to one embodiment of the present invention, and showing longitudinally ribs on an inner surface of the marker deployer tube, the ribs extending along substantially the full length of a marker disposed in the tube, and the ribs extending proximally of the marker.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

FIGS. 1-9 are included to provide context with respect to the present invention. It will be understood that the present invention may be used with, but is not limited to the features and elements shown and described with respect to FIGS. 1-9

Figure 1:
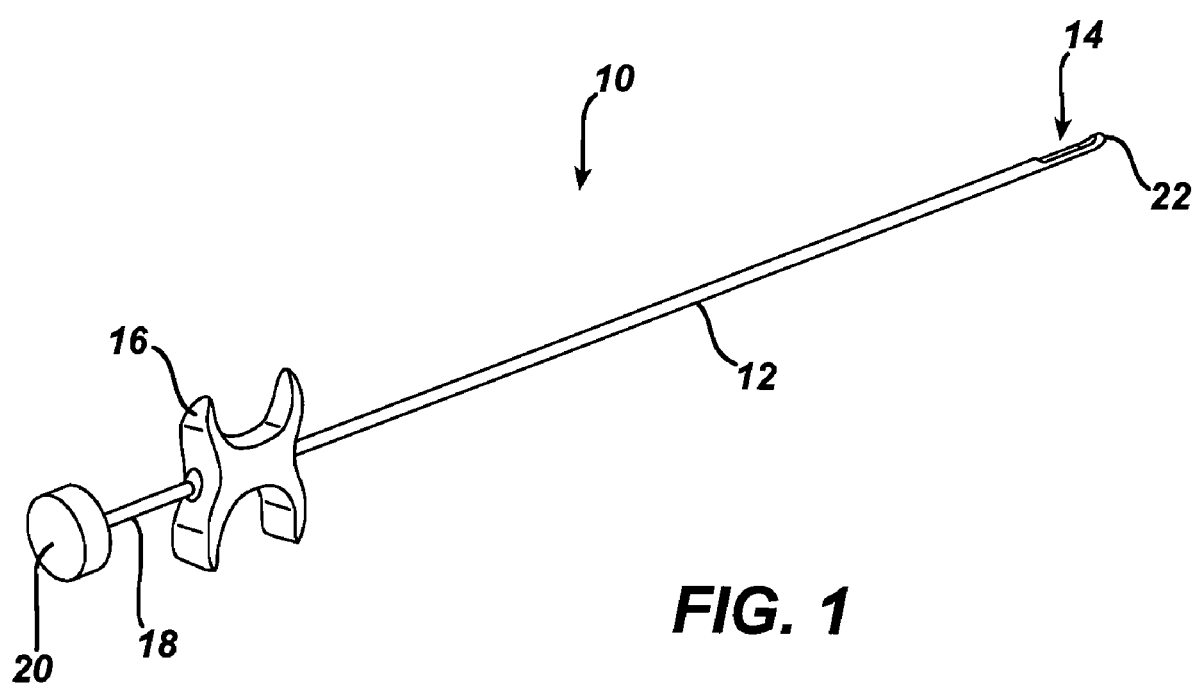
FIG. 1 depicts a perspective view of a marker delivery device of the type illustrated in U.S. patent application Ser. No. 12/196,301 filed Aug. 22, 2008.
Figure 2:
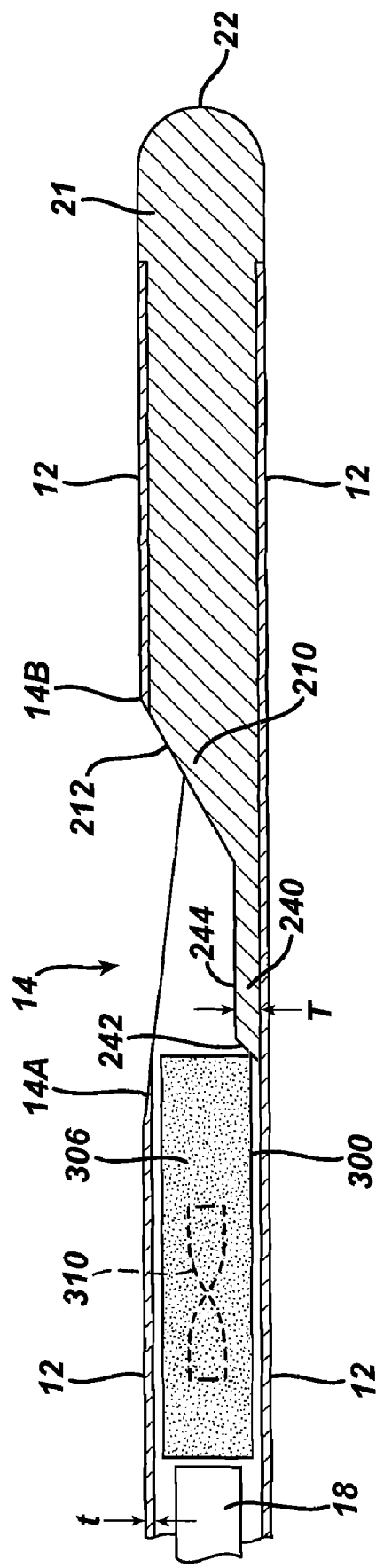
FIG. 2 depicts a cross-sectional view of a distal portion of a marker delivery device of the type illustrated in U.S. patent application Ser. No. 12/196,301 filed Aug. 22, 2008.
Figure 3:
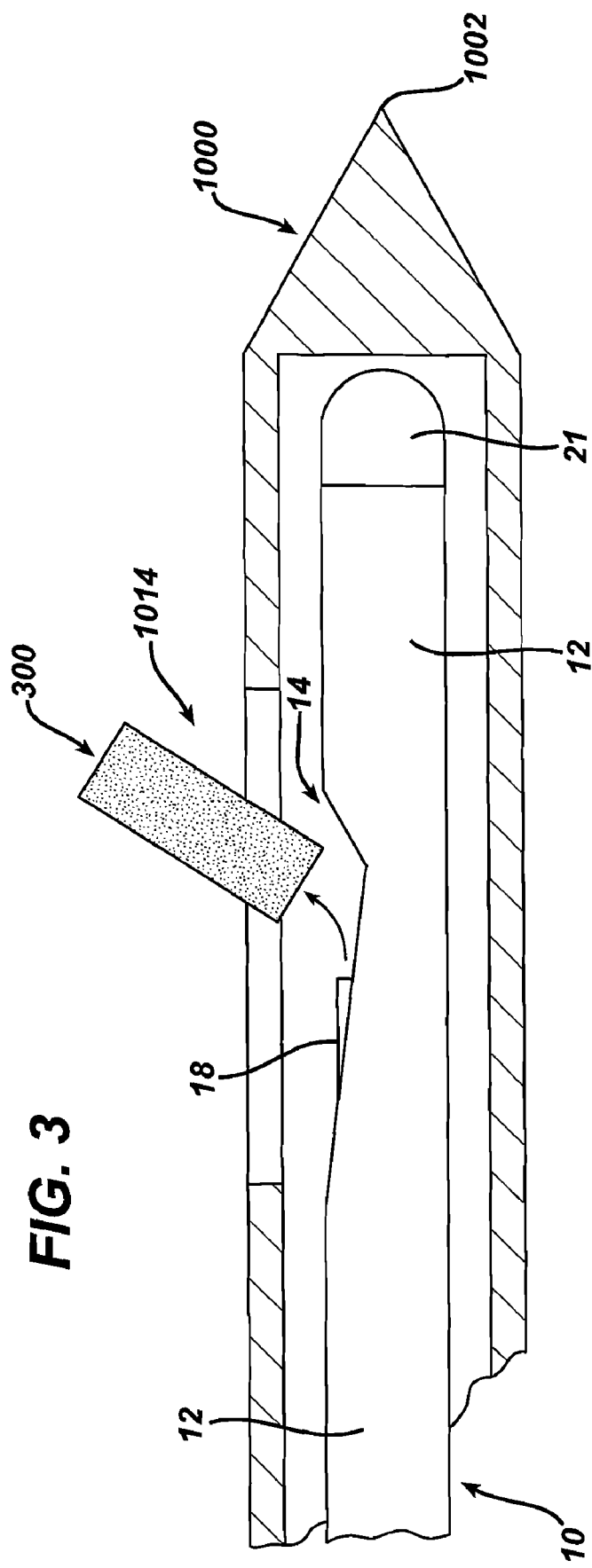
FIG. 3 depicts a marker being deployed from a deployer and through a lateral tissue receiving port in a biopsy needle to mark a biopsy site, such as illustrated in U.S. patent application Ser. No. 12/196,301 filed Aug. 22, 2008.

FIGS. 1-3 illustrate a marker delivery device 10 of the type illustrated in U.S. patent application Ser. No. 12/196,301 filed Aug. 22, 2008.

FIGS. 4-9 illustrate a marker deliver device of the type illustrated in U.S. patent application Ser. No. 12/563,360 filed Sep. 21, 2009.

A marker delivery device 10 may include a tubular elongate outer cannula 12 having a marker exit, such as side opening 14 formed near to, but spaced proximally from, the distal end of the cannula 12.

A grip 16 can be provided at the proximal end of cannula 12. A pushing member in the form of a push rod 18 can be provided, with push rod 18 extending coaxially in cannula 12 such that the push rod 18 is configured to translate within cannula 12 to displace one or more markers through the side opening 14 (see FIG. 2). Rod 18 can have a proximal portion (proximal portion 18A in FIG. 7) have sufficient rigidity in compression to push a marker from the internal lumen of cannula 12 out through opening 14, and include a more distal portion (for example portion 18B in FIG. 7) that is relatively flexible in bending so that the cannula 12 can be inserted along a curved path to deploy a marker element at a biopsy site.

A plunger 20 can be provided at the proximal end of rod 18 for forcing rod 18 distally in cannula 12 to deploy a marker out of the cannula 12. A user may grasp grip 16 with two fingers, and may push on plunger 20 using the thumb on the same hand, so that the marker delivery device 10 can be operated by a user's single hand. A spring (not shown) or other feature may be provided about rod 18 to bias rod 18 proximally relative to grip 16 and cannula 12.

FIG. 2 depicts a cross-sectional view of a distal portion of the marker delivery device 10. FIG. 2 shows a biopsy marker 300 disposed in the internal lumen 15 of the cannula 12. The marker 300 can comprise a biodegradable or otherwise resorbable body 306, such as a generally cylindrically shaped body of collagen, and a metallic, generally radiopaque marker element 310 (shown in phantom) disposed within or otherwise carried by the body 306.

The cannula 12 can be formed of any suitable metallic or non-metallic material. In one embodiment, the cannula 12 is formed of a thin walled hollow tube formed of a suitable medical grade plastic or polymer. One suitable material is a thermoplastic elastomer, such as Polyether block amide (PEBA), such as is known under the tradename PEBAX. The cannula 12 can be formed of PEBAX, and can be substantially transparent to visible light and X-ray.

The side opening 14 can be formed by cutting away a portion of the wall of cannula 12. The side opening 14 communicates with an internal lumen 15 of the cannula. The side opening 14 can extend axially (in a direction parallel to the axis of the lumen 15) from a proximal opening end 14A to a distal opening end 14B, as illustrated in FIG. 2.

The distal tip 22 extending from the distal end of cannula 12 can be rounded as shown in FIG. 2. Referring to FIG. 2, a marker delivery device can have the distal end of the cannula 12 closed by a unitary endpiece 21 formed in place in the distal end of the cannula 12, with a part of the endpiece 21 extending into the internal lumen 15 of the cannula. The distal endpiece 21 can be a molded or cast component, and can optionally provide an integrally formed combination of the tip 22, a ramp 210 having a ramp surface 212, and a marker engaging element 240. The ramp surface 212 aids in directing the marker 300 from the internal lumen 15 through side opening 14. The marker engaging element 240 may optionally be employed to retain the marker 300 in the internal lumen 15 until the user intends to deploy the marker.

The marker engaging element 240 may be disposed within the internal lumen 15, and at least a portion of the marker engaging element is disposed distally of the proximal end 14A of side opening 14. The marker engaging element 240 can extend along a portion of the floor of the cannula 15 under the opening 14, and the marker engaging element 240 can be positioned to reinforce the portion of the cannula in which the opening 14 is formed. For instance, by positioning the marker engaging element 240 underneath the opening 14, as shown in FIG. 2, the element 240 can help to stiffen the cannula 12 in the region where wall of the cannula 12 is cut to form the opening 14. In FIG. 2, the marker engaging element 240 extends from the proximal most portion of ramp surface 212, and does not extend proximally of the side opening 14, though in other embodiments, a portion of the element 240 could extend proximally of the opening 14.

In the embodiment shown in FIG. 2, marker engaging element 240 is in the form of a step having a generally uniform thickness T along the element's axial length, except that the element has a tapered proximal end 242. The tapered proximal end 242 can form an included angle with the longitudinal axis of the lumen 15 (included angle with a horizontal line in FIG. 2) of about 45 degrees, while the ramp surface 212 can form an included angle with the longitudinal axis of about 30 degrees.

The thickness T can be greater than the wall thickness t of the cannula 12, and in one embodiment T is at least about twice the thickness t. In one embodiment, the thickness T can be between about 0.018 inch to about 0.040 inch, and the wall thickness t can be between about 0.005 inch to about 0.008 inch. The internal diameter of lumen 15 can be about 0.120 inch.

In FIG. 2, the upwardly facing surface 244 (surface facing the opening 14) marker engaging element 240 extends distally to contact the ramp surface 212, so that there is not a space or gap between the surface 244 and the ramp surface 212. Such an arrangement is advantageous to reduce the possibility that the marker 300, upon moving past the marker engaging element, will become lodged between the marker engagement element and the ramp.

If desired, the marker engaging element 240, ramp 210, and/or the tip 22 can be formed of, or include, a material that is relatively more radiopaque than the wall of the cannula 12. For instance, where the element 240, ramp 210, and tip 22 are formed as an integral endpiece 21, the endpiece 21 can include a radiopaque additive, such as barium sulfate. For instance, the endpiece 21 can be a component molded of PEBAX, with about 20 percent by weight barium sulfate added to the molten PEBAX mold composition.

The relatively more radiopaque marker engaging element 240, ramp 210, and tip 22 can be useful in distinguishing the position of those components using radiographic imaging. Also, where the ramp and/or step of engaging element are positioned in association with the opening 14, the addition of a radiopaque material can help identify the position of the opening, and the position of the marker 300 relative to the opening before, during, or after deployment of the marker.

Only one marker is shown disposed in lumen 15 in the figures. However, it will be understood that multiple markers can be disposed in marker delivery device 10, such as in an end to end configuration. The markers can have the same size and shape, or alternatively have different sizes and/or shapes.

The cannula 15 can be generally transparent to visible light and x-ray, and the endpiece 21 can be generally opaque to visible light and x-ray. If desired, the endpiece 21 can be colored with a dye or other suitable colorant in the liquid mold composition. For example, it may be desirable to have different size markers (e.g. length and/or diameter) for different biopsy procedures. For instance, it may be desirable to provide a larger marker if a relatively large biopsy sample is taken, and a smaller marker if a relatively small biopsy sample is taken. The endpiece 21 can be colored using one of multiple colors to indicate the size of the marker disposed in the cannula. For instance, if three marker sizes are provided, the endpiece 21 can be colored one of three colors to identify which of the marker sizes are disposed in the cannula of a particular marker device. The endpiece 21 can also be colored to indicate a particular size (diameter or length) biopsy needle with which the marker delivery device is to be used. Additionally, multiple marker delivery devices could be packaged in kit form, with the kit including marker delivery devices having different size markers and correspondingly colored endpieces.

Referring to FIG. 3, the marker delivery device 10 may be used to deploy a marker to mark a particular location within a patient. In FIG. 3, a cannular biopsy needle 1000 is shown. The needle 1000 is shown having a closed distal end with piercing tip 1002, and a lateral tissue receiving aperture 1014. Marker deployer 10 may be introduced to a biopsy site through biopsy needle 1000, which can be the same needle used to collect a tissue sample from the biopsy site. The biopsy needle 1000 can be of the type used with single insertion, multiple sample vacuum assisted biopsy devices. Several such biopsy devices are disclosed in the various patents and patent applications that have been referred to and incorporated by reference herein, though other biopsy devices may be used.

FIG. 3 shows the distal end of a marker deployer 10 disposed within the needle 1000. The needle 1000 can be positioned in tissue, and a biopsy sample can be obtained through opening 1014, thereby providing a biopsy cavity adjacent opening 1014. Then, after the tissue sample has been obtained and transferred proximally through the needle, and without removing the needle 1000 from the patient's tissue, the deployer 10 can be inserted into a proximal opening in the needle 1000. In FIG. 3, the needle 1000 and deployer 10 are positioned such that opening 14 of cannula 12 and opening 1014 of needle 1000 are substantially aligned axially and circumferentially. Then, with the deployer and needle so positioned at the biopsy site, the push rod 18 can be advanced to deploy the marker up the ramp surface 212, through the opening 14, and then through opening 1014, into the biopsy cavity.

In some instances, it may be necessary to bend or otherwise flex the marker deployer cannula 12 and push rod 18 when inserting the deployer into the biopsy device. By reducing the effective contact surface area between the outer surface of the push rod 18 and the inner surface of the cannula 12, the tendency of the push rod 18 to "lock" within the cannula 12 may reduced and/or eliminated.

Figure 4:
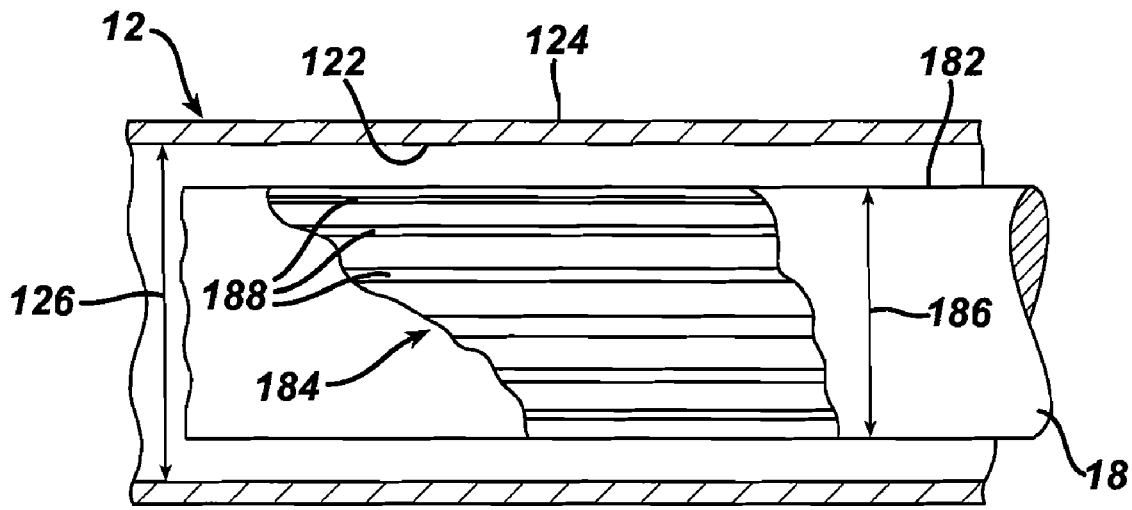
FIG. 4 depicts a portion of a marker deployer as shown in U.S. patent application Ser. No. 12/563,360 filed Sep. 21, 2009, where the inner diameter of the tube is generally smooth, and to reveal a member, such as a push rod, the push rod having a surface feature effective for reducing the contact surface area between a portion of the push rod disposed within the deployment tube and the inner surface of the deployment tube FIG. 5. Depicts a cross-section of the pushing member of FIG. 4 and illustrating the peaks of the elevated portions of the longitudinally extending ribs in relation to the diameter of the pushing member and in relation to the recessed portions of the outer surface of the push rod.
Figure 5:
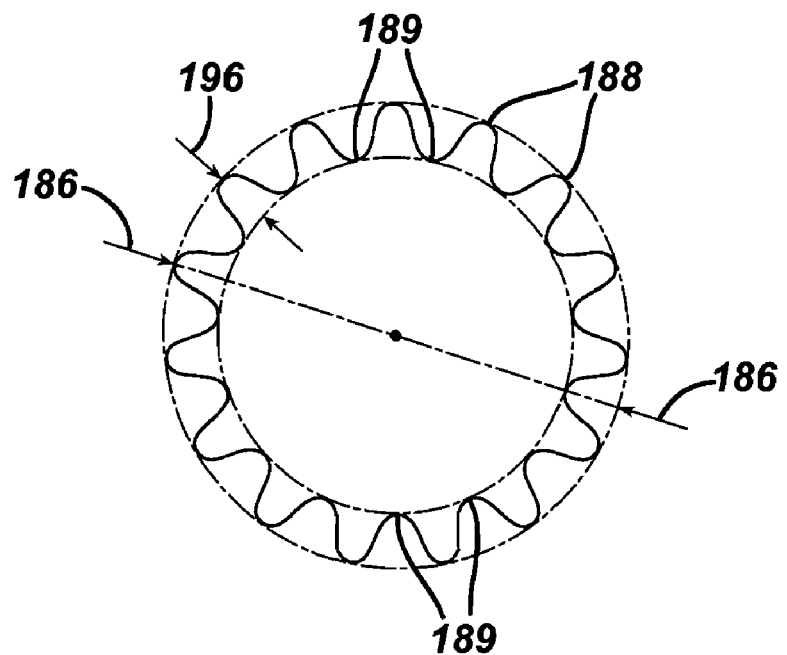
Figure 6:
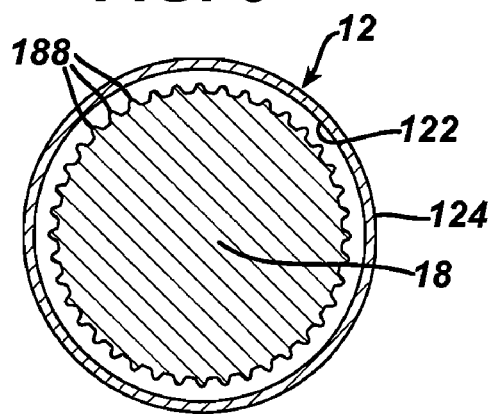
FIG. 6 depicts a cross-section of the deployer of FIG. 4 with the pushing member shown disposed within the deployer tube, and illustrating the circumferential peak to peak spacing of adjacent longitudinally extending ribs can be greater than the radial height of the ribs.

FIG. 4 illustrates a portion of a deployer tube and push rod. FIG. 5 illustrates a cross-sectional illustration of the push rod 18. FIG. 6 illustrates a cross-section of the push rod 18 disposed within the cannula 12.

In FIG. 4, a portion of the cannula 12 and push rod 18 are illustrated, with part of the cannula 12 cut away to show the push rod 18 disposed within the cannula 12. The cannula 12 can be formed from a thin wall, flexible non-metallic tube having a generally smooth outer surface 124, a generally smooth inner surface 122, and having an inner diameter designated 126 in FIG. 4. A generally flexible, elongate pushing member, such as a portion of push rod 18, is disposed at least partially within the internal lumen of the hollow cannula 12. The push rod 18 has an outer diameter designated 186 in FIG. 4.

In FIG. 4, push rod 18 is illustrated having an outer surface 182 that has a surface feature designated generally as 184, which surface feature is effective for reducing the contact surface area between the outer surface of the push rod 18 and the inner surface of the lumen extending through cannula 12 when the cannula 12 and rod 18 are bent or otherwise flexed. In one embodiment, the surface feature 184 is configured to be effective in providing at least about a 50 percent reduction (still more particularly at least about 75% reduction) in the contact surface area that would otherwise occur for a push rod 18 and cannula 12 both having generally smooth, untextured surfaces and the same nominal outer diameter and inner diameter.

In the embodiment shown in FIG. 4, surface feature 184 is shown comprising a plurality of longitudinally extending elevated portions in the form of ribs 188. The ribs 188 extend along at least a portion of the push rod 18 disposed within cannula 12.

For marker deployers 10 useful in connection with breast biopsy devices having a breast biopsy needle, and useful for deploying breast biopsy markers from breast biopsy devices, the inner diameter 126 of the lumen of cannula 12 may be (but is not limited to) at least about 0.08 inch, and the outer diameter 186 of the push rod 18 may be (but is not limited to) between about 0.04 inch and about 0.09 inch.

In one embodiment, the ribs 188 can have a radial height 196 measured with respect to adjacent recessed portions (designated as valleys 189) of between about 0.0001 inch and about 0.01 inch. More particularly, the ribs 188 can have a radial height of between about 0.0003 inch and about 0.004 inch, yet more particularly, the radial height 196 can be between about 0.0005 inch and about 0.004 inch. In one non-limiting example, the radial height 196 can be between about 0.001 inch and about 0.003 inch, such as about 0.002 inch plus or minus 0.001 inch. The radial height 196 can be less than one tenth of the diameter 186 of the push rod, and more particularly less than about one twentieth of the diameter 186. The radial height 196 can be less than one half (less than 50 percent of), and more particularly less than about one quarter of the difference between outer diameter 186 and the inner diameter 126 of the lumen of the cannula 12.

The number and size of longitudinal surface features may be selected to be effective in reducing the effective contact surface area between push rod and the inner surface of the cannula, without interfering with sliding of the push rod within the lumen of the cannula. For instance, but without being limited by theory, in one embodiment the push rod 18 may have at least about 20 ribs spaced around it's circumference, and less than about 100 ribs. The ribs can be formed by extruding, molding, or other suitable methods. The circumferential spacing between adjacent ribs can be greater than the radial height 196 of the adjacent ribs.

Figure 7:
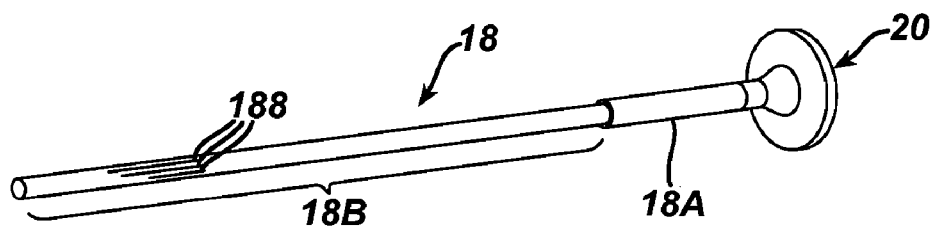
FIG. 7 illustrates a pushrod having a relatively rigid proximal portion 18A (such as stiffened by a metal sleeve) and a relatively flexible distal portion 18B comprising a plurality of longitudinally extending ribs.

FIG. 7 illustrates a push rod 18 having a relatively stiff proximal section 18A, and a flexible portion 18B comprising a plurality of ribs 188 as described above. The relatively stiff proximal portion 18A can comprise a metallic sleeve or other stiffening member disposed at the proximal end of the rod to prevent the proximal end of the push rod from bending or kinking when plunger 20 is pressed to deploy a marker. The flexible portion 18B may comprise ribs 188 or other surface features along some or substantially all the length of flexible portion 18B such as to be effective in preventing locking of the push rod 18 within cannula 12 when the rod and cannula are bent or otherwise disposed along a curved path.

Figure 8:
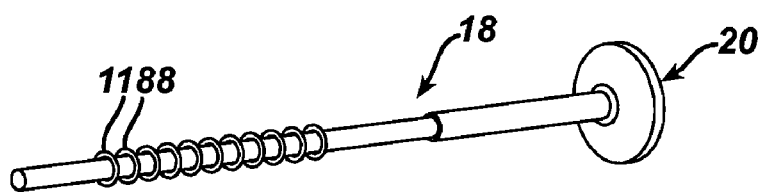
FIG. 8 illustrates a plurality of ring like ribs as described in U.S. patent application Ser. No. 12/563,360 filed Sep. 21, 2009.

FIG. 8 illustrates an alternative embodiment comprising surface features 1188 disposed at spaced apart locations along the length of the push rod 18. The surface features 1188 may be in the form of longitudinally spaced apart raised rings extending circumferentially around the diameter of push rod 18. The rings may be circumferentially continuous or formed of discrete segments. In yet another alternative embodiment, the outer surface of the push rod 18 may comprise surface features in the form of bumps or protrusions, such as bumps or protrusions having the radial height characteristics set forth above. The bumps or protrusions may be randomly positioned on the surface of the rod 18, or may be arranged in a predetermined pattern.

Figure 9:
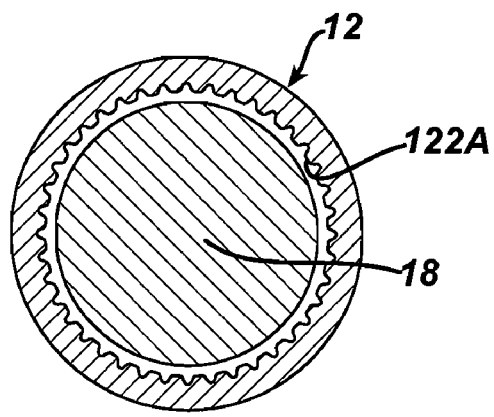
FIG. 9 illustrates a marker deployer embodiment as described in U.S. patent application Ser. No. 12/563,360 filed Sep. 21, 2009.

FIG. 9 illustrates the cannula 12 having an inner surface 122A having a surface feature effective for reducing binding/locking of the rod 18 within the cannula 12.

Referring to FIGS. 10-14, in one non-limiting aspect, the present invention provides a marker delivery device having a hollow tube configured to engage a marker along at least a portion of the length of the marker, and more particularly, along substantially the full length of the marker. In another non-limiting aspect, the present invention provides a marker deliver device having a hollow tube configured to engage a marker at spaced apart locations around an outer surface of the marker.

Figure 10:
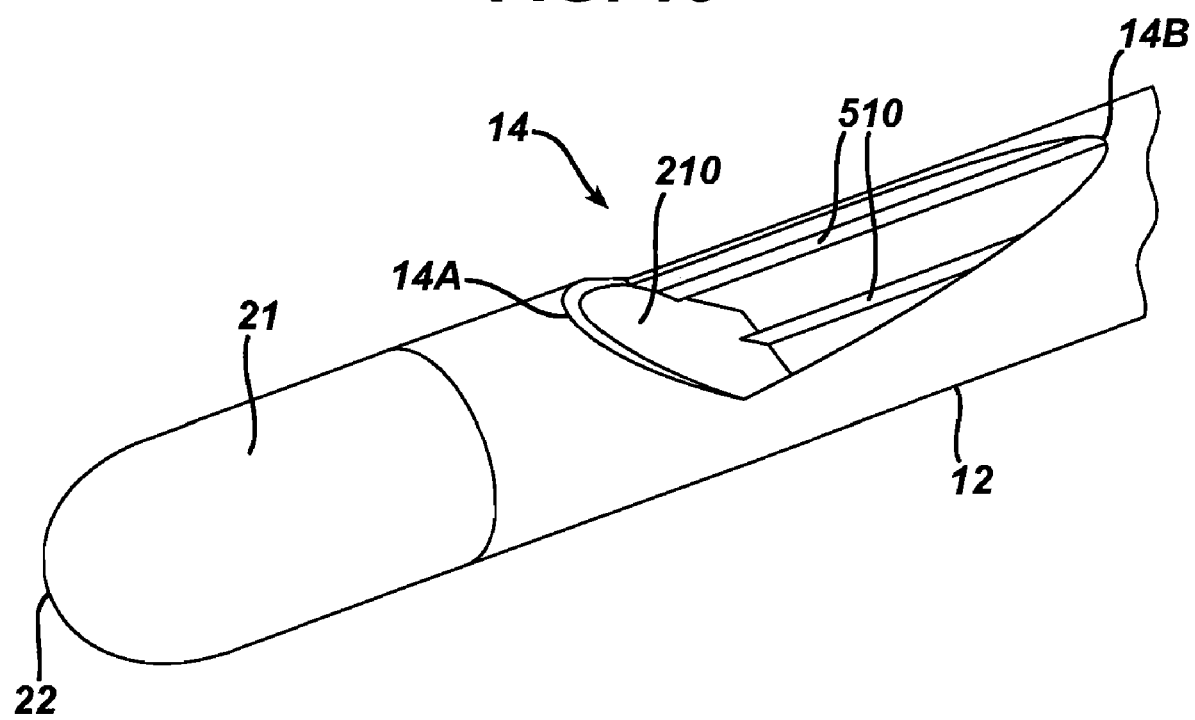
FIG. 10 is a schematic illustration showing a distal portion of a biopsy marker delivery device according to one embodiment of the present invention, with longitudinally extending ribs visible through a side marker exit.

FIG. 10 illustrates the distal portion of a biopsy marker delivery device according to one embodiment of the present invention. The device is shown comprising a tubular elongate outer cannula 12 having a marker exit in the form of a side opening 14 formed near to, but spaced proximally from, the distal end of the cannula 12. The cannula 12 can comprise a thin wall hollow tube formed of a suitable medical grade plastic or polymer, and side opening 14 communicates with an internal lumen of the cannula. The side opening 14 is shown extending axially (longitudinally) from a proximal opening end 14A to a distal opening end 14B. A unitary endpiece 21 may be used to close the distal end of the cannula 12, and may include a rounded distal tip 22.

Still referring to FIG. 10, a ramp 210 is visible through side opening 14. In addition, a plurality of inner surface features, such as in the form of longitudinally extending ribs 510, are visible through side opening 14. Each longitudinally extending rib can have a length longer than the axial length of the marker 300, and each rib may engage a marker 300 along substantially the full length of the marker 300 prior to the marker being deployed from side opening 14.

Figure 11:
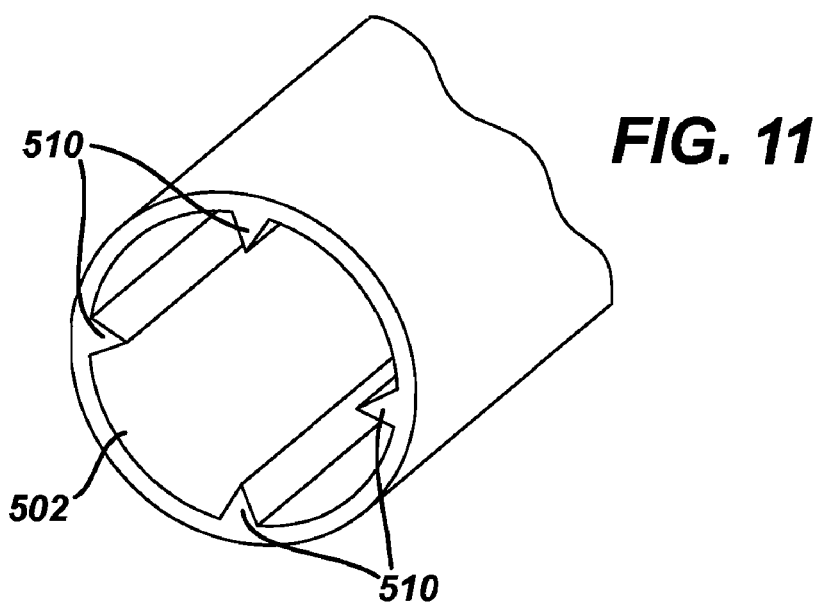
FIG. 11 is a schematic partial cross-sectional illustration of a biopsy marker delivery device according to an embodiment of the present invention, including a deployer tube having four ribs extending longitudinally along an inner surface of the tube and the ribs extending radially inward from an inner surface of the tube.

FIG. 11 provides a cross-sectional illustration of the cannula 12, such as taken at a position proximal of the end 14B of the side opening 14. In FIG. 11, the cannula tube 12 is shown including four generally equidistantly spaced apart ribs 510, the ribs 510 being spaced circumferentially around the inner surface 502 of the tube 12. In FIG. 11, the ribs are shown spaced apart at substantially 90 degree intervals around the circumference of the inner surface 502 of the tube 12.

Figure 12:
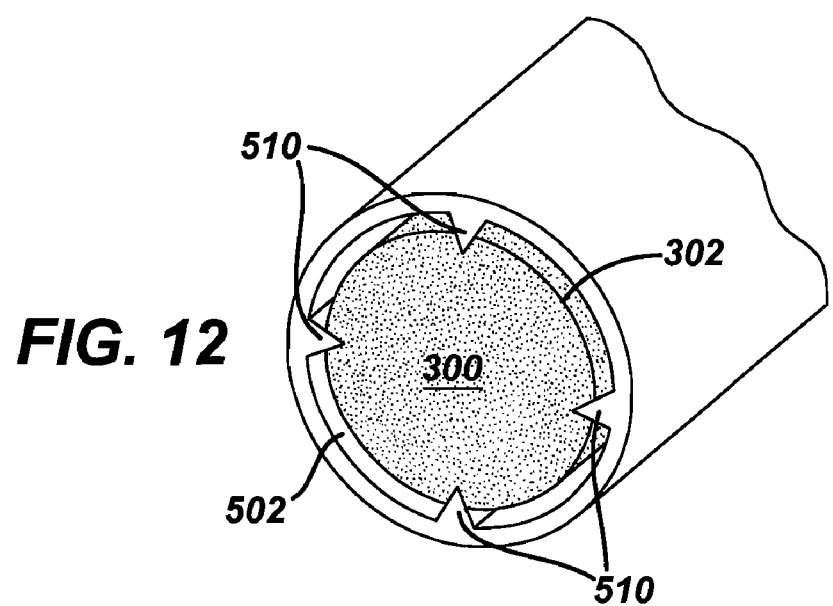
FIG. 12 is a schematic partial cross-sectional illustration of the biopsy marker delivery device of FIG. 11 with a biopsy marker shown disposed in the deployer tube, and showing four internal ribs engaging the biopsy marker at four generally equidistantly spaced apart locations around the circumference of the outer surface of the biopsy marker.
Figure 13:
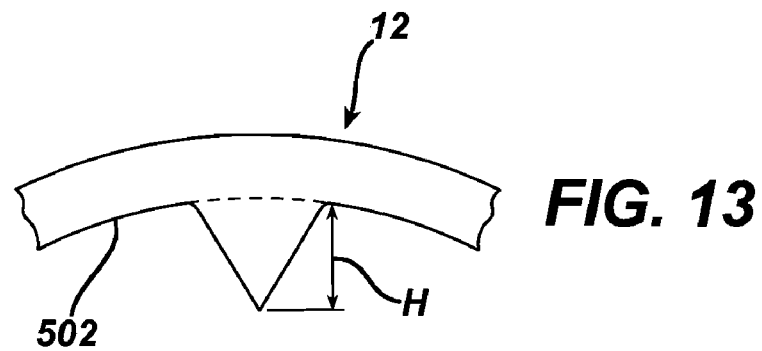
FIG. 13 is a schematic illustration of a cut away portion of a deployer tube illustrating of the height "H" of a rib.

FIG. 12 shows a marker 300 disposed within the inner lumen of tube 12, and also illustrates engagement of the ribs 510 with an outer cylindrical surface 302 at four spaced apart locations. The height H (FIG. 13) of the ribs 510 can be selected to ensure all four of the ribs 510 simultaneously engage the marker 300.

The height H can extend radially inwardly from surface 502 a distance of between about 0.010 inch and about 0.050 inch from the internal surface of the internal lumen. The radial height H can be between about 5 percent about 20 percent of the internal diameter of the internal lumen.

By way of example, the inner diameter of the tube can be between about 0.080 inch and about 0.150 inch, and the height H can be between about 0.010 to about 0.025 inch. In one non limiting embodiment, the inner diameter of the cannula can be about 0.120 inch, the nominal outer diameter of the marker 300 can be about 0.098 inch, and the height H can be about 0.015 inch.

The longitudinally extending ribs 510 are shown extending proximally from the ramp 210 in FIG. 11 and FIG. 14. The ribs 510 may extend the full length of the cannula tube 12, and may be formed by extrusion. The ribs 510 can extend proximally of the proximal most marker 300 in the tube 12, and the ribs can engage the full axial length of the marker 300 as the marker 300 is pushed distally through the tube. FIG. 14 illustrates ribs 510 extending proximally of a marker 300 disposed in cannula tube 12. Accordingly, the ribs may provide an engaging force, which may be in the form of a frictional force against the marker 300, to assist in preventing premature marker deployment. Additionally, the ribs 510 may be employed to reduce frictional forces between the push rod 18 and the inner wall of the cannula 12.

Embodiments of the devices disclosed herein are generally designed to be disposed of after a single use, but could be designed to be used multiple times. After forming the marker, and inserting the marker into the deployer, the biopsy device can be sterilized. The device can be placed in a package, such as plastic or TYVEK bag.

The packaged biopsy device may then be placed in a field of radiation such as gamma radiation, x-rays, or high-energy electrons to sterilize the device and packaging. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. Accordingly, the scope of the present invention should be considered in terms of the following claims and is understood not to be limited to the details of structure and operation shown and described in the specification and drawings.

What is claimed is:

1. A biopsy delivery device comprising:
    a hollow tube having a proximal end, a distal end, an internal lumen having an internal surface, and a lateral marker exit;
    a distal endpiece affixed to the distal end of the hollow tube, wherein the lateral marker exit is proximal of the distal endpiece; and
    at least one biopsy marker having an axial length, the at least one marker disposed within the internal lumen of the hollow tube proximal of the lateral marker exit, the at least one marker deployable from the tube through the lateral marker exit;
    wherein the hollow tube comprises at least one pair of internal protrusions, each having a longitudinal length, wherein the longitudinal length of each protrusion is greater than the axial length of the at least one biopsy marker, wherein each protrusion engages the at least one marker and extends along at least a portion of the length of the at least one marker disposed within the internal lumen, wherein one protrusion of the at least one pair of internal protrusions has a first longitudinal length, wherein another protrusion of the at least one pair of internal protrusions has a second longitudinal length, and wherein the first longitudinal length is different from the second longitudinal length.

2. The biopsy device of claim 1 wherein each internal protrusion extends along substantially the full length of the at least one marker.

3. The biopsy device of claim 1 wherein at least one internal protrusion extends proximally of the at least one marker.

4. The biopsy device of claim 3 wherein the at least one internal protrusion extends proximally from the marker exit along substantially the full length of the internal lumen.

5. The biopsy device of claim 1 comprising a plurality of internal protrusions spaced circumferentially around the internal surface of the tube.

6. The biopsy device of claim 1 comprising a plurality of radially inwardly extending protrusions.

7. The biopsy device of claim 1 comprising at least three protrusions extending radially inwardly to engage the at least one marker element.

8. The biopsy device of claim 7 wherein the at least three protrusions extend axially such that at least a portion of each of the at least three protrusions extend proximally of the at least one marker element.

9. The biopsy device of claim 1 wherein the tube comprises at least three longitudinally extending internal ribs, and wherein the at least three ribs engage the at least one marker at at least three circumferentially spaced apart locations.

10. The biopsy device of claim 9 wherein the at least three longitudinally extending ribs extend proximally of the at least one marker.

11. The biopsy device of claim 1 comprising at least four longitudinally extending ribs.

12. The biopsy device of claim 1 comprising at least three circumferentially spaced apart protrusions associated with the internal lumen, wherein the at least three circumferentially spaced apart protrusions extend radially inwardly from an internal surface of the internal lumen.

13. The biopsy device of claim 12 wherein the protrusions extend radially inwardly a distance of between about 0.010 inch and about 0.050 inch from the internal surface of the internal lumen.

14. The biopsy device of claim 12 wherein the protrusions have a radial height of between about 5 percent and about 20 percent of the internal diameter of the internal lumen.

15. A biopsy delivery device comprising:
    a generally flexible hollow tube having a proximal end, a distal end, a side marker exit, and an internal lumen having an internal surface, and at least three circumferentially spaced apart protrusions associated with the internal surface of the hollow tube, wherein the at least three circumferentially spaced apart protrusions define at least three circumferentially spaced apart regions, wherein at least a first of the at least three circumferentially spaced apart protrusions is disposed on a portion of the internal surface of the internal lumen opposite the side marker exit;
    a pushing member disposed at least partially within the internal lumen of the hollow tube; and
    at least one biopsy marker disposed within the hollow tube distal of the pushing member and deployable from the hollow tube upon advancement of the pushing member within the hollow tube;
    wherein the at least three circumferentially spaced apart protrusions extend radially inwardly from the internal surface of the internal lumen and engage the at least one marker.

16. The biopsy delivery device of claim 15 wherein each of the at least three circumferentially spaced apart protrusions comprises a triangular shaped ridge.

17. The biopsy device of claim 15 wherein at least a second of the at least three circumferentially spaced apart protrusions extends distally of the at least one marker.

18. A biopsy delivery device comprising:
- a generally flexible hollow tube having a proximal end, a distal end, a lateral marker exit disposed proximal of the distal end, and an internal lumen having an internal surface, and a plurality of circumferentially spaced apart protrusions associated with the internal surface of the hollow tube;
- a pushing member disposed at least partially within the internal lumen of the hollow tube; and
- at least one biopsy marker disposed within the hollow tube distal of the pushing member and deployable from the hollow tube upon advancement of the pushing member within the hollow tube;
- wherein at least one of the plurality of circumferentially spaced apart protrusions extends longitudinally on the internal surface of the internal lumen to a first point distal of a proximal edge of the lateral marker exit, wherein the first point is longitudinally disposed between the proximal edge of the lateral marker exit and a distal edge of the lateral marker exit, and wherein at least one other of the plurality of circumferentially spaced apart protrusions extends longitudinally on the internal surface of the internal lumen to a second point proximal of the proximal edge of the lateral marker exit.

19. The biopsy delivery device of claim 18 wherein the plurality of circumferentially spaced apart protrusions extends proximally of the at least one biopsy marker.

20. The biopsy delivery device of claim 18 wherein the plurality of circumferentially spaced apart protrusions are configured to engage a portion of the at least one biopsy marker.

* * * * *